United States Patent [19]

Melly et al.

[11] Patent Number: 5,059,397
[45] Date of Patent: Oct. 22, 1991

[54] GAS DETECTOR SYSTEM

[75] Inventors: Jeffrey Melly, Clayton, Mo.; Shawn Bennett, Cumberland, R.I.

[73] Assignee: Watlow/Winona, Inc., Winona, Minn.

[21] Appl. No.: 310,631

[22] Filed: Feb. 15, 1989

[51] Int. Cl.⁵ .............................................. G01N 21/01
[52] U.S. Cl. ...................... 422/94; 250/429; 250/432 R; 250/435; 250/504 R; 324/464; 324/466; 356/51; 356/437; 356/438; 422/98; 436/133; 436/149
[58] Field of Search ............... 422/94, 98; 250/429, 250/432 R, 435, 504 R; 324/464, 466; 356/51, 437, 438; 436/133, 149

[56] References Cited

U.S. PATENT DOCUMENTS

| | | | |
|---|---|---|---|
| 3,753,656 | 8/1973 | Matson et al. | 422/89 |
| 3,765,842 | 10/1973 | Purt | 422/89 |
| 3,840,341 | 10/1974 | Rogers | 436/133 |
| 3,854,876 | 12/1974 | Rankine et al. | 436/133 |
| 4,277,438 | 7/1981 | Ejzak | 436/133 |

Primary Examiner—Robert J. Warden
Assistant Examiner—Timothy M. McMahon
Attorney, Agent, or Firm—Hugh D. Jaeger

[57] ABSTRACT

A gas detector system for detecting gases such as $CO_2$. Sample air is passed through a critically sized sealed sample chamber in a sample cell. Infrared waves are generated in an insulated heater assembly, and radiate through windows of the sealed sample chamber concurrent with the sample air. The strength and magnitude of the infrared waves is attenuated by the level of gas, such as $CO_2$, present in the sample air passing through the critically sized sealed sample chamber, and is sensed by a thermopile detector, including a filter for a specific frequency of infrared energy. Electronic circuitry processes the thermopile signal and measures other parameters of the gas detector to provide a signal indicative of the percentage of gas concentration in the air. Extensive use of insulation about and around the thermopile detector electronic circuitry and other components of the detector maximize stability and reliability.

17 Claims, 6 Drawing Sheets

GAS DETECTOR SYSTEM

BACKGROUND OF THE INVENTION

1. Field of the Invention

The present invention pertains to a gas detector system, and more particularly, pertains to a detector for the detection of gas, such as $CO_2$, in a sample cell by a thermopile assembly where extensive thermal insulation of the component parts promotes stability of the detector and its components. A summing circuit sums four signals to derive a signal indicative of $CO_2$ concentration in the gas.

2. Description of the Prior Art

Prior art systems were susceptible to any variation in the heater temperature which caused large variations in the detector output. If the heater temperature changes, there is less or more infrared energy. The detector measures this as a change in the amount of $CO_2$ in the gas chamber, so monitoring the heater temperature is very critical and this was not previously done.

Prior art systems have also used comparative techniques of a chopper wheel with moving mechanical components to switch from a known $CO_2$ cell to an unknown $CO_2$ cell, and then derive the concentration by the different readings between the two cells.

The present invention overcomes the disadvantages of the prior art by providing a gas detector system which has thermal stability and is not effected by ambient changes, a lower wattage heater source, and a lower circuit gain, thereby minimizing noise in the system.

SUMMARY OF THE INVENTION

The general purpose of the present invention is a gas detector system for the detection of $CO_2$ or other gas concentration in air samples which are passed through a sample cell. Infrared energy waves, produced in an insulated electrical resistance heater coil assembly, pass through the sample cell with the sample gases, and are attenuated when $CO_2$ gases are present. The amount of attenuation is sensed through an optical band pass filter in front of a thermally insulated thermopile detector. Attenuation information is processed by thermally insulated electronic circuitry to determine the quantity of the gas in the sample cell. Temperature sensing elements provide temperature data at selected points for processing by the electronic circuitry. Insulation is provided around and about the thermopile detector, the electric resistance heater coil, and between the thermopile detector and electronic resistance heater coil and the electronic circuitry. $CO_2$ gas detection is by way of example and for purposes of illustration only and not to be construed as limiting of the present invention.

According to one embodiment of the present invention, there is provided a gas detector system with a base structure with a series of aligned components secured thereto. An inverted "U" shaped sample cell secures to the base structure by angled gas inlet and outlet nipples which lead to a horizontally aligned cylindrical chamber through vertical members of the sample cell. A sapphire window affixes in an annular groove at each end of the cylindrical cell with silicone O'rings to seal the cylindrical chamber. An insulated electrical resistance heater coil and a thermocouple align along the longitudinal axis at one end of the sample cell to emit infrared energy into the sample cell. An insulated detector housing aligns at the opposing end of the sample cell to sense infrared energy being emitted through the horizontally aligned cylinder chamber by the insulated electrical resistance heater coil. Insulation engages around and about strategic components to provide component temperature stability of the gas detector system. Electronic circuitry is insulated from the sample cell, the thermopile assembly and the insulated detector housing by insulation disposed vertically therebetween. Insulation is also located between the base structure and the circuit board for further temperature stability.

One significant aspect and feature of the present invention is a gas detector system with an insulated electrical resistance heater coil and an insulated detector housing.

Another significant aspect and feature of the present invention is a gas detector system with an insulated electrical resistance heater coil and an insulated thermopile assembly aligned at opposing ends of a sample cell. There is also insulation beneath the electrical circuit board. An insulator is also placed vertically between the circuit board and the aligned sample cell.

Another significant aspect and feature of the present invention is a cylindrical detector chamber with coaxially aligned sapphire windows near the chamber ends.

Another significant aspect and feature of the present invention is the use of an optical band pass filter with a thermopile detector for the particular gas being sensed. Other filters can be utilized to sense other gases. The heater temperature and the cell geometry can also be changed to sense other gases.

Another significant aspect and feature of the present invention is the use of temperature sensing devices for use in conjunction with electronic circuitry for determination of the gas concentration. This includes a thermocouple embedded into the insulated electrical resistance heater coil.

Having thus described one embodiment of the present invention, it is a principal object hereof to provide a gas detection system.

One object of the present invention is a gas detection system which can detect a particular gas dependent upon the system parameters and calibration. This particular gas detection system as disclosed is for detecting $CO_2$ gas, and with a change in system parameters and calibration, other gases could be sensed.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
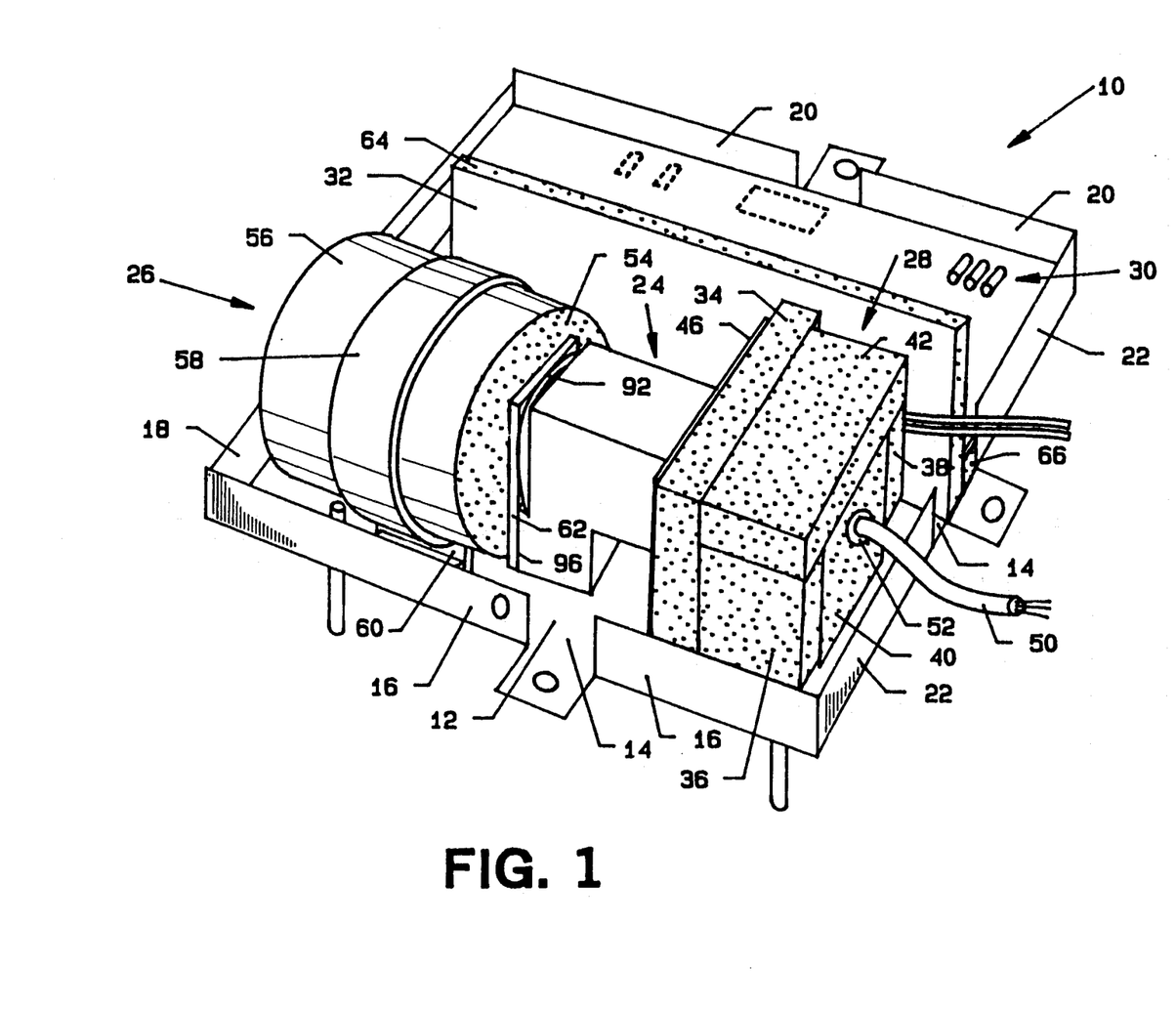
FIG. 1 illustrates a perspective view of a gas detector system.

FIG. 1 illustrates a perspective view of a gas detector system 10, the present invention, for use in detection of carbon dioxide gas concentrations, by way of example and not to be construed as limiting of the present invention. A flanged base plate 12 includes a bottom 14, and continuous or non-continuous sides 16, 18, 20 and 22 as illustrated extending vertically from the bottom 14. Other illustrated components and assemblies mounted on or about the flanged base plate 12 include a centrally aluminum inverted "U" shaped sample cell 24, an electrical resistance heater coil assembly 26 aligned with the aluminum sample cell 24, a detector housing insulation assembly 28 aligned with the aluminum sample cell 24, a horizontally aligned electronics circuit board 30, and a shiny vertically aligned chromed metal baffle 32 extending upwardly from the bottom 14 disposed between the circuit board 30 and the detector housing insulation assemblies 28.

Figure 2:
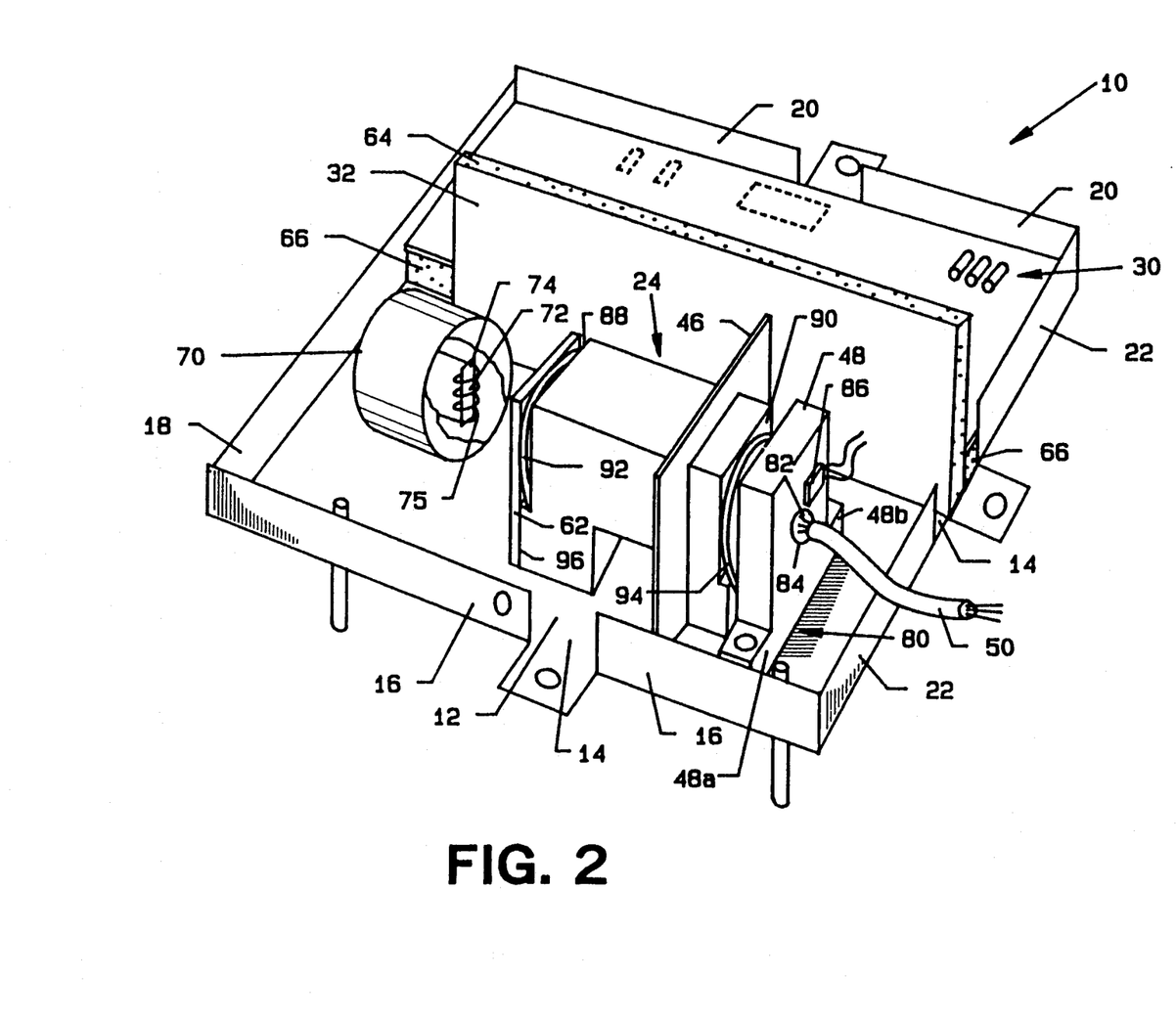
FIG. 2 illustrates a perspective view of a gas detector system with removed layers of insulation.

Insulation layers are strategically placed throughout and within various structures of the gas detector system 10 to enhance component temperature stability. The detector housing insulation assembly 28 contains a plurality of thermal insulation members including an inner vertical insulation member 34, side vertical insulation members 36 and 38, an outer vertical end vertical insulation member 40, and a horizontal top insulation member 42. A vertically aligned "U" shaped bracket plate 46 fits over the aluminum sample cell 24, and is a backing plate for the inner vertical insulation member 34. The detector housing insulation assembly 28 covers, insulates and provides thermal protection for a detector housing 48 as illustrated in FIG. 2. An electronics wire cable 50 extends through a hole 52 in the outer vertical end insulation member 40 and attaches to a temperature transducer 86 on the detector housing.

Figure 4:
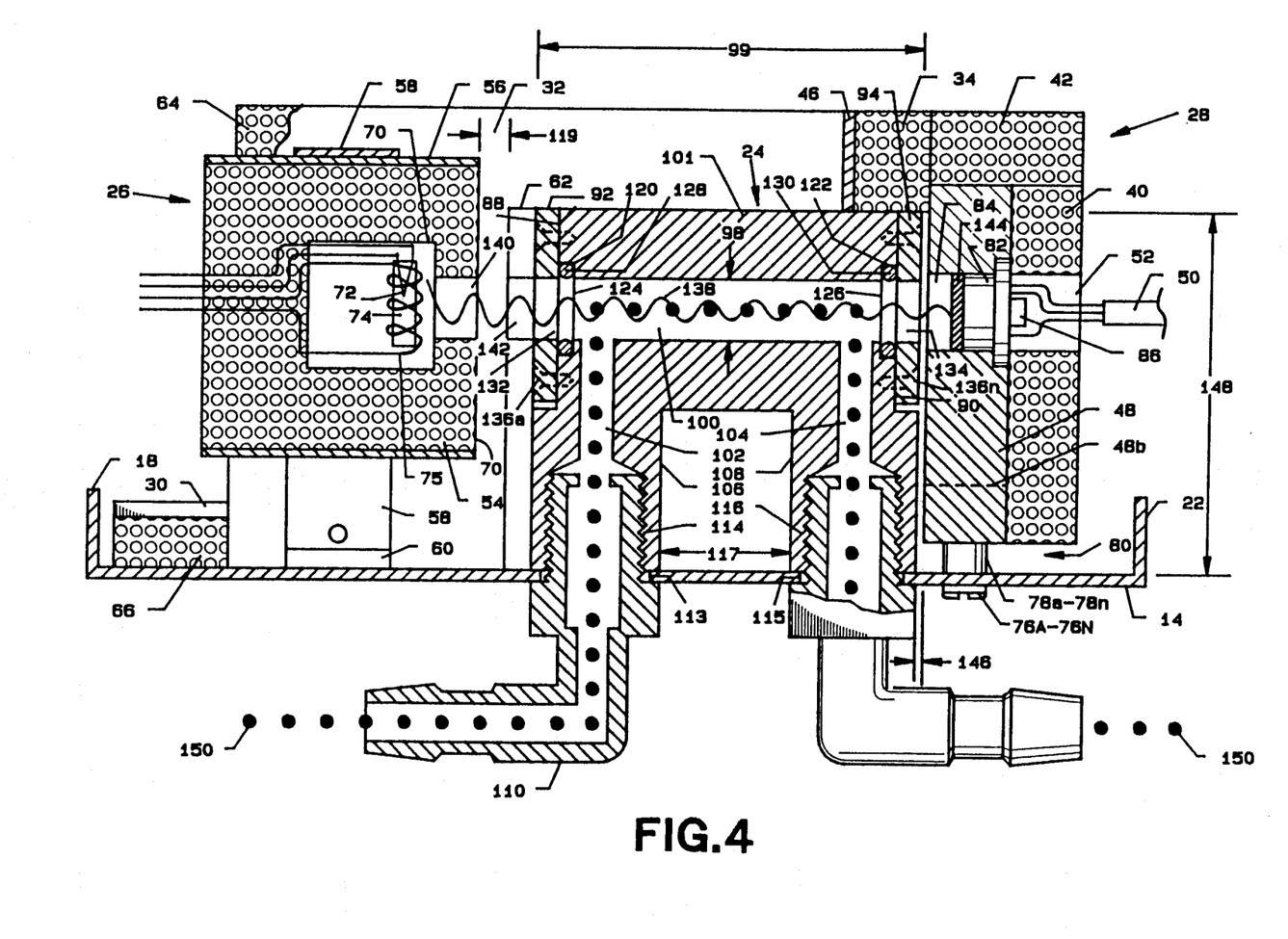
FIG. 4 illustrates a cross-sectional view of the gas detector system taken along line 4—4 of FIG. 3.

The electrical resistance heater coil assembly 26 includes cylindrically shaped ceramic fiber insulation 54 measuring approximately 1½" in length and 1¼" in diameter which is secured by a chromed segmented cylinder 56 and an overlying band clamp 58. The ceramic fiber insulation 54 includes a mixture of aluminum oxide, silicon oxide and binders. The band clamp 58 is secured to the base plate bottom 14 by a bracket 60. The ceramic fiber insulation 54 surrounds an encapsulated heater coil as illustrated in FIGS. 2 and 4. A planar layer of ceramic fiber insulation 62 secures vertically to a vertical face of the sample cell 24, and is later described in detail.

Other strategically placed areas of insulation include a planar layer of insulation 64 affixed to the back side of the polished metal baffle 32 and another planar layer of insulation 66 between the circuit board 30 and the base plate bottom 14.

FIG. 2 illustrates a perspective view of the gas detector system 10 with the detector housing insulation assembly 28, ceramic fiber insulation 54 and assorted components removed for purposes of illustration to reveal the detector housing 48 and a ceramic body 70. The ceramic body 70, measuring approximately ⅞" in length and ½" in diameter, consists of $Al_2O_3$, other oxides, binders and a ceramic cement. A type "N" thermocouple 72 is embedded in a subcore 74 of MgO, $AL_2O_3$ or similar core material, and is surrounded by an electrical resistance heater coil 75. The subcore 74, including the type "N" thermocouple 72 and the surrounding electrical resistance heater coil 75, are entirely encased within the ceramic body 70.

The detector housing 48 secures to the base plate bottom 14 by a plurality of fasteners 76a-76n of FIG. 4 inserted through the base plate bottom 14 and through a plurality of spacers 78a-78n of FIG. 4, and into the mounting shoulders 48a-48b of the detector housing 48 to provide an insulated air gap 80 between the base plate bottom 14 and lower surface of the detector housing 48 as illustrated in FIG. 4. The spacers 78a-78n are nylon material to prevent thermal conductivity. A thermopile detector 82 secures in a horizontally aligned hole 84 centrally located in the detector housing 48, and includes an electronic wire cable 50 which attaches to the circuit board 30. A temperature probe 86 mounts on the outer vertical face of the detector housing 48 adjacent to the thermopile detector 82 in the hole 84.

The aluminum sample cell 24 secures to the base plate bottom 14 as later described in detail and aligns between the detector housing 48 and the ceramic body 70 and its associated components. The aluminum sample cell 24, a cross section of which is illustrated in FIG. 4, is essentially an inverted "U" shaped structure. Vertically aligned recessed surfaces 88 and 90 at the upper outer ends of the sample accommodate washer like sample cell caps 92 and 94. The ceramic fiber insulation 62 aligns and secures to the outer surface of the sample cell cap 92 and the lower vertically aligned surface 96 of the aluminum sample cell 24. The "U" shaped bracket plate 46 is illustrated aligned over the aluminum sample cell 24.

Figure 3:
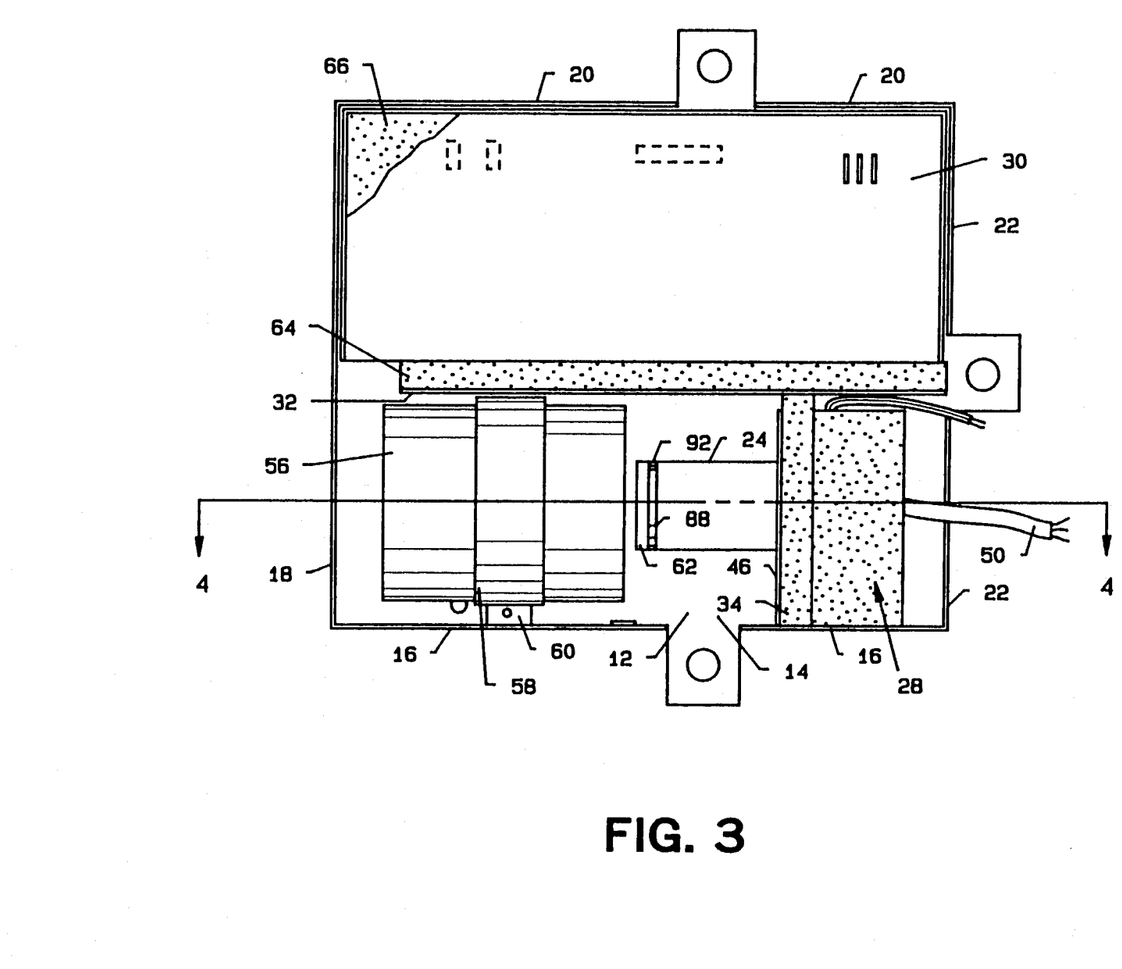
FIG. 3 illustrates a top view of the gas detector system.

FIG. 3 illustrates a top view of the gas detector system 10 where all numerals correspond to those elements previously described.

FIG. 4 illustrates a cross section taken along line 4—4 of FIG. 3 where all numerals correspond to those elements previously described. Illustrated in particular is the aluminum sample cell 24 and its associated attendant components. A cylindrical chamber 100 with a dimension length 99 of 1.550" and a dimension diameter 98 of 9/32" aligns horizontally within the horizontal portion 101 of the aluminum sample cell 24 along the longitudinal axis to which a number of components align, including the thermopile detector 82, the electrical resistance heater coil assembly 26, the ceramic fiber insulation 62, the sample cell caps 92 and 94, and other components as now described. The detector in this example is a Dexter Research Model 2M with a 4.3u bandpass filter and argon back filled. Any other suitable detector could be utilized with similar operation characteristics. The holes 132 and 134 in the sample cell caps 92 and 94 are included in the overall length dimension 99 of the cylindrical chamber 100 which measures 1.550". The relationship of the cylinder chamber 100 diameter to the cylinder length, including the sample cell cap holes 132 and 134 is relevant, and is later described in further detail in the Mode of Operation. Vertically aligned cylindrical holes 102 and 104 located in the vertical members 106 and 108 of the aluminum sample cell 24 intersect the cylindrical chamber 100. Threaded plastic nipples 110 and 112 pass through holes 113 and 115 in the base plate bottom 14, and screw into threaded holes 114 and 116 in the bottoms of the vertical members 106 and 108 to secure the aluminum sample cell 24 to the flanged base plate 12, and to provide an inlet and outlet path for sampled gas. The spacing 117 between the vertical members 106 and 108 is 0.550". Annular grooves 120 and 122 align coaxially with the longitudinal axis and with the extremes of the cylindrical chamber 100. Sapphire windows 124 and 126 secure to the inner surfaces of the annular grooves 120 and 122 by silicone O'rings 128 and 130. The sample cell caps 92 and 94 align along the longitudinal axis and include central holes 132 and 134, respectively, and secure as later described against the silicone O'rings 128 and 130, and against the recessed surfaces 88 and 90 of the aluminum sample cell 24 to seal sapphire windows 124 and 126 to the cylindrical chamber 100. A plurality of securement fasteners 136a–136n pass through the sample cell caps 92 and 94 and through recessed surfaces 88 and 90 into the aluminum sample cell 24. The spacing 119 between the electrical resistance heater coil assembly 26 and the ceramic fiber insulation 62 is approximately 0.240". Infrared energy waves 138 are illustrated passing through a ¼" deep circular recess 140 in the ceramic fiber insulation 54, through the hole 142 in the ceramic fiber insulation 62, through the hole 132 in the sample cell cap 92, through the sapphire window 124, through the cylindrical chamber 100, through the sapphire window 126, through the hole 134 in the sample cell cap 94, into the hole 84, and through an optical band pass filter 144 to be sensed by the thermopile detector 82. The optical band pass filter 144 only allows energy at the 4.3 micron energy level to pass through. In this example, the filter band pass is 4.3 microns for $CO_2$ gas. For any other gases, different band pass filters would be utilized. The detector housing 48 is spaced by dimension 146 measuring 0.030" from the aluminum sample cell 24. The height 148 of the top of the aluminum sample cell 24 above the base plate bottom 14 is 1.375". The dimensions are by way of example and for purposes of illustration only, and not to be construed as limiting of the present invention. The dimensions can be determined and sized depending upon the specific application and measurement of the specific gas. Sampled $CO_2$ gas particles 150 are illustrated flowing through the angled plastic nipple 110, the cylindrical hole 102, the cylindrical chamber 100, the cylindrical hole 104 and the angled plastic nipple 112 to be sensed in the cylindrical chamber 100 where it impinges upon or interferes with the infrared waves 138 emitted from the ceramic body 70. The interference effect of the $CO_2$ gas particles 150 with the infrared waves 138 is cumulative from left to right in the cylindrical chamber 100, and is depicted by decreasing amplitude of the infrared energy waves 138 traveling from the left to the right. The sample gas particles 150 can pass in either direction through the cylindrical chamber 100 depending on the point of introduction of the sample gas, whether it be introduced and pressure fed into angled plastic nipples 110 or 112.

Figure 5:
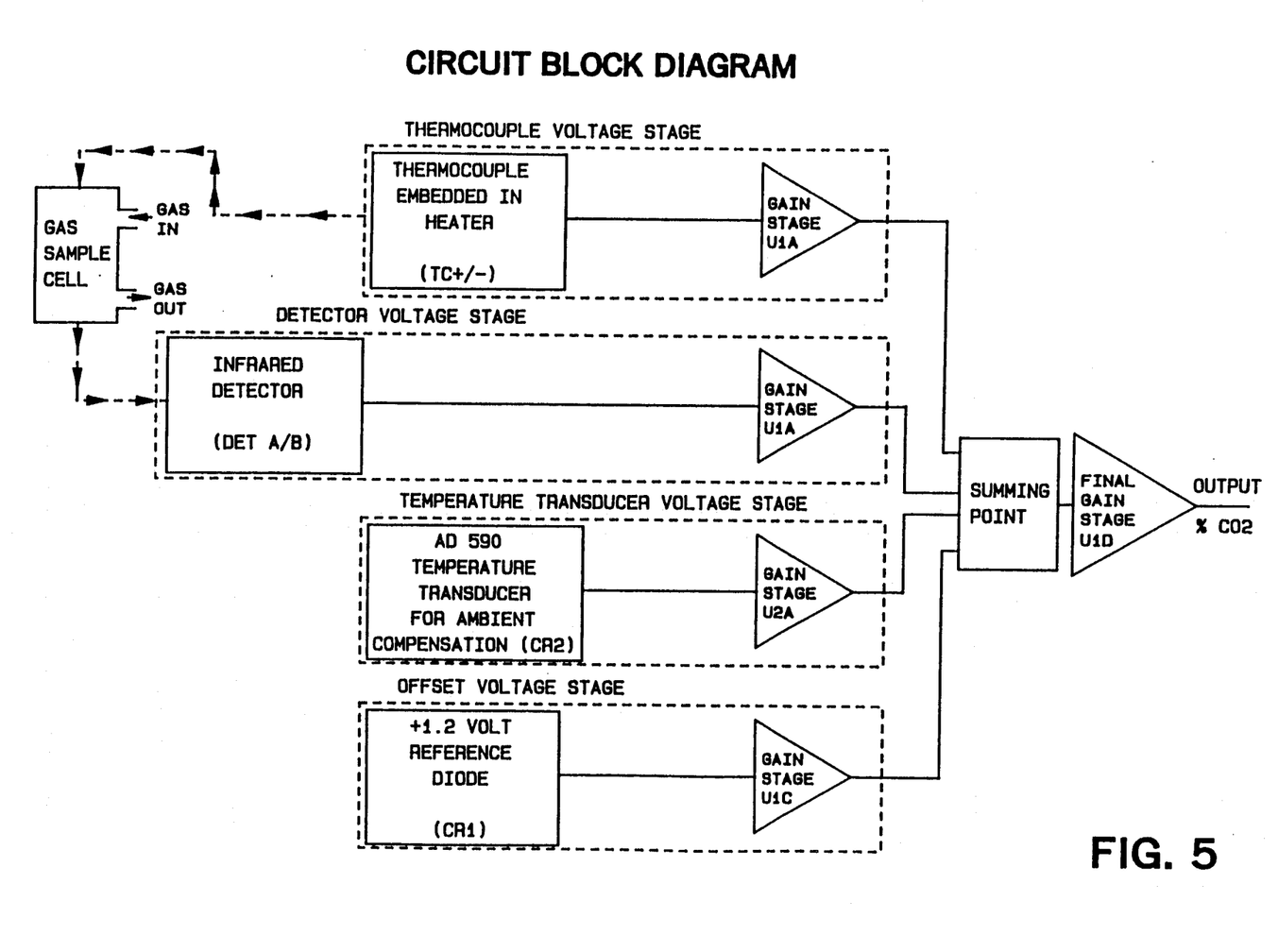
FIG. 5 illustrates a block diagram for the electrical circuit.

FIG. 5 illustrates a block diagram of the gas detector system of four stages of electrical circuitry, including a thermocouple voltage stage, a detector voltage stage, a temperature transducer voltage stage, and an offset voltage stage where the voltages are summed at a common summing point.

Figure 6:
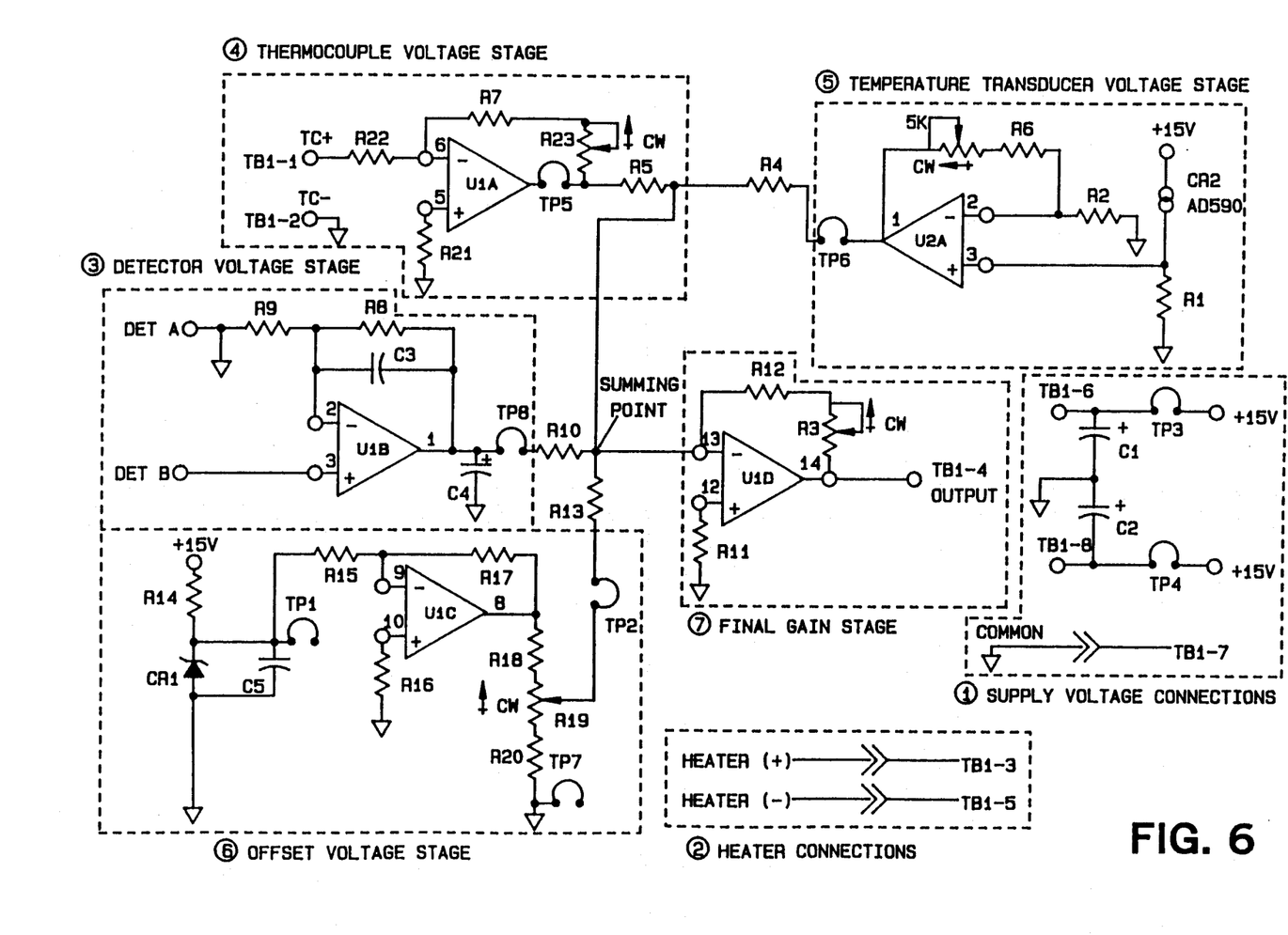
FIG. 6 illustrates an electrical circuit schematic diagram for the gas detector system.

FIG. 6 illustrates the electrical circuit schematic diagram of the gas detector system 10. The schematic is divided into 7 sections as shown in FIG. 6.

1. The "Supply Voltage Connections" section provides (through TB1-6, TB1-7 and TB1-8) an input for the + and −15 volt supply voltages and common needed to operate the gas detector system. The section also contains C1 and C2 which eliminate any unwanted noise on the incoming supply lines.

2. The "Heater Connections" section provides an input of the +5V supply voltage required to operate the heater assembly contained in the gas detector system. This section consists of two connectors, TB1-3 and TB1-5.

3. The "Detector Voltage Stage" section is one of the most important of the seven sections. The purpose of this section is to amplify the signal received from the thermopile detector. This signal is inversely related to the amount of $CO_2$, by example, in the gas sample cell. This section consists of: Input pads DET A and DET B to accept the signal from the thermopile detector, operational amplifier U1B which amplifies the signal, resistors R8 and R9 which determine the gain of amplifier U1B, C3 which determines the speed of U1B, and C4 which eliminates any unwanted noise coming out of U1B. The representative gain for this example is about 430.

4. The "Thermocouple Voltage Stage" section accepts a voltage from the thermocouple embedded in the heater. The purpose of this section is to generate a voltage which corresponds to the heater temperature, and feed it back into the system to eliminate any changes in the output due to heater temperature fluctuations. These fluctuations could be caused by supply voltage change, air currents, heater aging, etc. This section consists of: TB1-1, and TB1-2, which accept the thermocouple input leads, operational amplifier U1A to amplify the thermocouple voltage and R7, R22, R21 and R23 which determine the gain of U1A. The gain is set during calibration and is determined by the heater temperature so that variations in heater temperature will not effect the system output.

5. The "Temperature Transducer Voltage Stage" section is for the purpose of monitoring the ambient temperature as seen by the thermopile detector. This section eliminates any changes in the system output due to changes in ambient temperature. This section includes: CR2 which is a temperature transducer (Analog Devices P/N AD590), which translates the temperature into a current, R1 which translates the current into a voltage, operational amplifier U2A which amplifies this voltage, and R2, R6 and R24 which determine the gain of U2A. The gain is set to compensate for variations in ambient temperature.

6. The "Offset Voltage Stage" section generates a constant voltage which is fed into the system to allow for calibration. This section consists of CR1 which is a temperature independent +1.2 volt reference diode, R14 which determines the current drawn through CR1, C5 which eliminates any unwanted noise, U1C which amplifies the 1.2 volts, R15, R16 and R17 which determine the gain of U1C, and R18, R19 and R20 which determine the amount of offset voltage to be applied to the system. The gain is set to "zero" and the system output at zero percent of the gas.

The output voltages from the "Detector Output Stage", the "Thermocouple Voltage Stage", the "Temperature Transducer Voltage Stage" and the "Offset Voltage Stage" are all summed together through summing resistors R4, R5 and R10 and R13. This summed voltage is at summing point A, and is applied to the "Final Gain Stage" section.

7. The "Final Gain Stage" section serves the purpose of amplifying the combined signals from the other four sections previously described. An operational amplifier U1D amplifies the signal. R11, R12 and R3 determine the gain of U1D. Connector TB1-4 provides the output of the entire system. The final gain stage is used to adjust and set the final system output for a predetermined percentage of the gas.

The output of the system is a non-linear voltage which corresponds to the percentage of the gas present in the sample cell. This voltage can be directly related to the percent of the gas by first using a voltage/percent curve, second by connecting the output directly into a microprocessor system with a lookup table, or third by linearizing the curve and reading the voltage directly. Other methods of relating the output voltage to percentage of the gas can be utilized as desired.

MODE OF OPERATION

The heater, at one end of the gas sample, operates at approximately 700° C. and generates infrared energy. A gas sample is pumped through the sample cell at approximately 3 to 7 liters per minute. Different flow rates can be utilized with the system as the system is calibrated for other flow rates. The gas sample is in direct line between the heater and the detector. The infrared energy, from the heater, passes through the sample cell, and is absorbed by the gas present. The amount of energy reaching the detector is inversely related to the amount of the gas in the sample cell. The detector in turn transforms the amount of energy it receives into a voltage which is then fed to the circuit for subsequent processing to output a signal representative of the gas percentage.

Various modifications can be made to the present invention without departing from the apparent scope hereof. Different flow rates can be utilized as required and depending upon the particular calibration of the system. Gases other than $CO_2$ can be sensed and the system is then calibrated accordingly.

We claim:

1. $CO_2$ gas detector analyzer system comprising:
   a. a gas sample cell with windows on each end;
   b. a heater including an embedded thermocouple position at one end of said cell;
   c. thermopile detector and a temperature transducer adjacent thereto at an other end of said cell; and,
   d. means for summing four voltages of said thermopile detector, an offset voltage state, said thermocouple and temperature transducer and means for generating a voltage signal from said summed voltages of said summing means corresponding to the percentage of $CO_2$ gas in said cell.

2. Gas detector analyzer system comprising:
   a. a gas sample cell with windows on each end;
   b. a heater including an embedded thermocouple position at one end of said cell;
   c. thermopile detector and a temperature transducer adjacent thereto at an other end of said cell; and,
   d. means for summing four voltages of said thermopile detector, an offset voltage stage, said thermocouple and temperature transducer and means for generating a voltage signal from said summed voltages of said summing means corresponding to the percentage of gas in said cell.

3. System of claim 2 wherein said heater coil is embedded in a cast ceramic body.

4. System of claim 3 wherein said cast ceramic body includes $Al_2O_3$, MgO, binders and cement.

5. System of claim 3 including a thermocouple in a ceramic core embedded in said heater coil.

6. System of claim 4 including ceramic insulation surrounding said cast ceramic body.

7. System of claim 2 including insulation between said cell and said heater.

8. System of claim 2 including a temperature transducer adjacent said thermopile detector.

9. System of claim 8 including insulation surrounding said thermopile detector and said temperature transducer.

10. System of claim 2 including a shiny metal member between said summing and generating means, and said heater, said cell, and said detector.

11. System of claim 2 including physically insulating said means for generating said summing from said heater.

12. System of claim 2 wherein said thermocouple is a type "N".

13. System of claim 2 including a band pass filter between said sample cell and said thermopile detector.

14. System of claim 13 wherein said band pass filter is 4.3 microns for $CO_2$ gas.

15. System of claim 2 wherein the diameter of said sample cell is 9/32 inches.

16. Process of measuring percentage of a particular gas in a sample cell comprising:
   a. passing gas including a particular gas through a sample cell;
   b. generating infrared energy in a heater assembly, including a thermocouple embedded in said heater assembly for generating a thermocouple signal, and directing said infrared energy to pass through said sample cell;
   c. detecting infrared energy at an other end of said cell with a thermopile detector, and generating a detector signal and including a temperature transducer immediately adjacent said thermopile detector for generating a transducer signal;
   d. summing a detector signal, said temperature transducer signal, said thermocouple signal, and an offset voltage signal; and,
   e. generating a signal corresponding to the percentage of the particular gas from said summed detector signal, said temperature transducer signal, said thermocouple signal and said offset voltage signal.

17. Process of claim 16 wherein said gas is $CO_2$.

* * * * *